US00PP33404P2

(12) United States Plant Patent
Austin

(10) Patent No.: US PP33,404 P2
(45) Date of Patent: Aug. 31, 2021

(54) SHRUB ROSE PLANT NAMED 'AUSCLERGY'

(50) Latin Name: *Rosa hybrida*
Varietal Denomination: AUSclergy

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/974,282

(22) Filed: Dec. 16, 2020

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./101, 102, 104
See application file for complete search history.

*Primary Examiner* — Susan McCormick Ewoldt
*Assistant Examiner* — Karen M Redden
(74) *Attorney, Agent, or Firm* — KPPB LLP

(57) ABSTRACT

A variety of rose plant of the shrub class, named 'AUSclergy'. The 'AUSclergy' is a variety of a very healthy and robust rounded medium sized rose shrub bearing fully open, medium large, almost flat rosettes of pure yellow having a medium-strong fruity fragrance with notes of apricot, green apple and honey.

1 Drawing Sheet

Classification: The present invention relates to a new *Rosa hybrida* shrub of the market class 'English Rose'.

Variety denomination: The new plant has the varietal denomination 'AUSclergy'.

ORIGIN OF INVENTION

This invention relates to a new and distinct variety of shrub rose plant named 'AUSclergy', which was originated from the cross-pollination of the two 'unnamed' and unpatented seedlings of *Rosa hybrida.*

BACKGROUND OF THE INVENTION

The primary objective of this breeding was to produce a very healthy and robust rounded medium sized rose shrub bearing fully open, medium large, almost flat rosettes of pure yellow having a medium-strong fruity fragrance with notes of apricot, green apple and honey.

SUMMARY OF THE INVENTION

Among the features which distinguish the new variety from others presently available and commercial rose cultivars known to the inventor is the following combination of characteristics: repeat flowering medium-large, double blooms of pure yellow with a very high quantity of thorns/prickles on the stems and having good disease resistance.

Asexual reproduction of the new variety by budding as performed in Albrighton, Britain shows that the foregoing and other distinguishing characteristics come true to form and are established and transmitted through succeeding asexual propagations. 'AUSclergy' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSclergy' are two unnamed seedlings. The new rose may be distinguished from its seed parent, by the following combination of characteristics: the seed parent is of a pink color compared to the yellow of 'AUSclergy' and has flowers of semi-double form. The new rose may be distinguished from its pollen parent, by the following combination of characteristics: the pollen parent is also of a pink color and has smaller blooms that are less disease resistant when compared to 'AUSclergy'.

COMPARISON WITH THE CLOSEST COMMERCIALLY AVAILABLE CULTIVAR

The closest commercially available cultivar to the new variety is 'AUSwalker' (U.S. Plant Pat. No. 8,678). While both blooms are yellow in color 'AUSwalker' has a significantly higher petal count. The bloom diameter of 'AUSwalker' is also larger than that of 'AUSclergy'. In addition, the growth habit of 'AUSwalker' is very tall and upright and may grow as a climbing rose while 'AUSclergy' in contrast is much shorter and more spreading. Finally, 'AUSclergy' has a significantly higher count of prickles when compared to 'AUSwalker'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSclergy' specimens were made at a nursery in Albrighton, Wolverhampton, United Kingdom. The following description is of 1 year-old rose plants of the new variety grown in a garden environment in Albrighton, Britain in the month of July. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2 cm long and 2 cm in diameter when the petals start to unfurl. Form: The bud form is pointed ovoid and broad based. Color: When sepals first divide, the bud color is predominantly RHS 150D (yellow-green group). When half blown, the upper sides of the petals are RHS 6B (yellow group), and the lower sides of the petals RHS 6B (yellow group). Calyx: Shape: star shape, with the sepals folding back against the stems. Length: 5 cm. Diameter: 5 cm. Sepals: Arrangement: Regularly arranged. Color: Upper Surface: RHS 137B (green group). Lower Surface: RHS 143A (green group). Length: 2.2 cm. Width: 0.6 cm. Shape: Lanceolate. Surface texture: Upper Surface: Downy. Lower Surface: Glandular. Number: There are 3 lightly appendaged sepals, and 2 unappendaged sepals with hairy edges. Receptacles: Color: RHS 143C (green group). Shape: Funnel. Size: Medium, about 1.0 cm long× 0.7 cm wide. Surface: Smooth. Peduncle: Length: Short, averaging about 6 cm. Surface: Prickly. Color: RHS 143C (green group). Strength: Strong.

*Blooms.*—Size: Medium, average open diameter is about 7 cm. Borne: Several together in clusters of 4-14 with blooms having a rounded shape. Stems: Strength: Strong, average length is about 40 cm. Diameter: 0.5 cm. Form: When first open, bloom is cupped. Permanence of bloom: retains its form to the end and the outer petal edges curl slightly. Flower Type: Double.

*Petalage.*—Number of petals under normal conditions: approximately 95. Color: The upper sides of the petals are RHS 2C (yellow group). The reverse sides of the petals are RHS 3B (yellow group). The base of the petals has a small basal spot that is RHS 5B (yellow group). Variegations: None. Discoloration: The general tonality at the end of the first day is RHS 6B (yellow group), and at the end of the third day is RHS 3B (yellow group). Fragrance: Moderate to strong. Character of fragrance: Fruity.

*Petals.*—Texture: Satiny. Size: Width: 1.2-1.5 cm. Length: 2 cm. Surface: Smooth. Shape: Obovate. Margin: Entire. Apex Shape: Rounded. Base Shape: Acute. Form: Incurved. Arrangement: Informal. Petaloids: Number: 0-10. Color: RHS 8B (yellow group). Length: 1.5 cm. Width: 0.4 cm. Shape: Obovate. Margin: Irregular. Persistence: Petals hang on and dry. Lastingness: On the plant: Fair about 4-7 days. As a cut flower: not tested.

*Reproductive parts.*—Stamens: Number: 15-20. Length: approximately 0.3 cm. Anthers: Length: approximately 0.2 cm. Color: RHS 5C (yellow group). Arrangement: Regular around styles. Filaments: Color: RHS 17C (yellow-orange group). Length: approximately 0.2 cm. Pollen: Color: RHS 17B (yellow-orange group). Amount: Scarce. Pistils: Number: approximately 60. Length: approximately 0.7 cm. Styles: Color: RHS 154D (yellow-green group). Length: approximately 0.7 cm. Stigmas: Color: RHS 15A (yellow-orange group). Length: approximately 0.1 cm. Hips: NONE Observed.

Plant characteristics:

*Plant form.*—Shrub.

*Plant growth.*—Vigorous and bushy.

*Age to maturity.*—2 years.

*Mature plant.*—Height: 110 cm. Width: 110 cm.

*Rootstock.*—*'Rosa dumetorum* 'Laxa' for the observed plants in the United Kingdom.

*Foliage.*—Number: Leaflets on normal mid-stem leaves is: 7 with instances of 5 (including terminal leaflet). Size: Small, about 10 cm long×6.5 cm wide. Quantity: Normal. Number of leaves per flowering stem is: 6-10. Color: New foliage: Upper side: RHS 137B (green group). Lower side: RHS 147B (yellow-green group). Old foliage: Upper side: RHS 147A (yellow-green group). Lower side: RHS 147B (yellow-green group).

*Leaflets.*—Size: About 3.5 cm long×2.5 cm wide. Shape: Pointed oval. Base Shape: Rounded. Apex Shape: Acuminate. Texture: Leathery. Glossiness: Medium glossiness. Edge: Serrated. Serrations: Single. Petiole: Color: RHS 146B (yellow-green group). Length: 3 cm. Width: 0.2 cm. Surface Texture: Glandular with prickles on the underside. Petiole Rachis: Color: RHS 146B (yellow-green group). Underside: Smooth with prickles. Stipules: Length: 2 cm, glandular. Color: RHS 146C (yellow-green group). Auricle: Shape: Lanceolate. Length: 0.5 cm. Width: 0.1 cm. Color: RHS 146C (yellow-green group). Vein Color: RHS 147A (yellow-green group). Venation Pattern: Reticulate.

*Wood.*—New Wood: Color: RHS 143C (green group). Bark: Smooth. Old Wood: Color: RHS 144B (yellow-green group). Bark: Smooth.

*Branching habit.*—Number: Approximately 1-2 per main stem. Dimensions: Length: 60-70 cm. Diameter: 0.6 cm.

*Stems.*—Mature Stem: Length: 80 cm. Diameter: 0.7 cm. Internode Distance: 5-6 cm. The above measurements are all variable, depending on growing conditions in a season. Stem Pubescence Present: No.

*Prickles.*—Quantity: On main canes from base: Many. Number per stem length: approximately 20 per 10 cm. On laterals from main canes: Many. Number per stem length: approximately 20 per 10 cm. Form: Deep concave (larger prickles). Length: Range from 0.6-1.1 cm. Color When Young: RHS 150B (yellow-green group). Color When Mature: RHS 151B (yellow-green group).

*Small prickles.*—Quantity: Main stalk: Many. Number per stem length 25 per 5 cm. Laterals: Many. Number per stem length: 25 per 5 cm. Color: When young: RHS 150B (yellow-green group). When mature: RHS 151B (yellow-green group).

*Disease resistance.*—Powdery Mildew (*Podosphaera pannosa*): Resistant. Downy Mildew (*Peronospora* species): Resistant. Blackspot (*Diplocarpon rosae*): Resistant. Rust (*Phragmidium tuberculatum*): Resistant.

*Pest resistance.*—Not tested.

*Winter hardiness.*—Not tested.

*Growing conditions.*—Normal garden conditions.

What is claimed is:

1. A new and distinct variety of shrub rose plant named 'AUSCLERGY', substantially as illustrated and described herein.

* * * * *

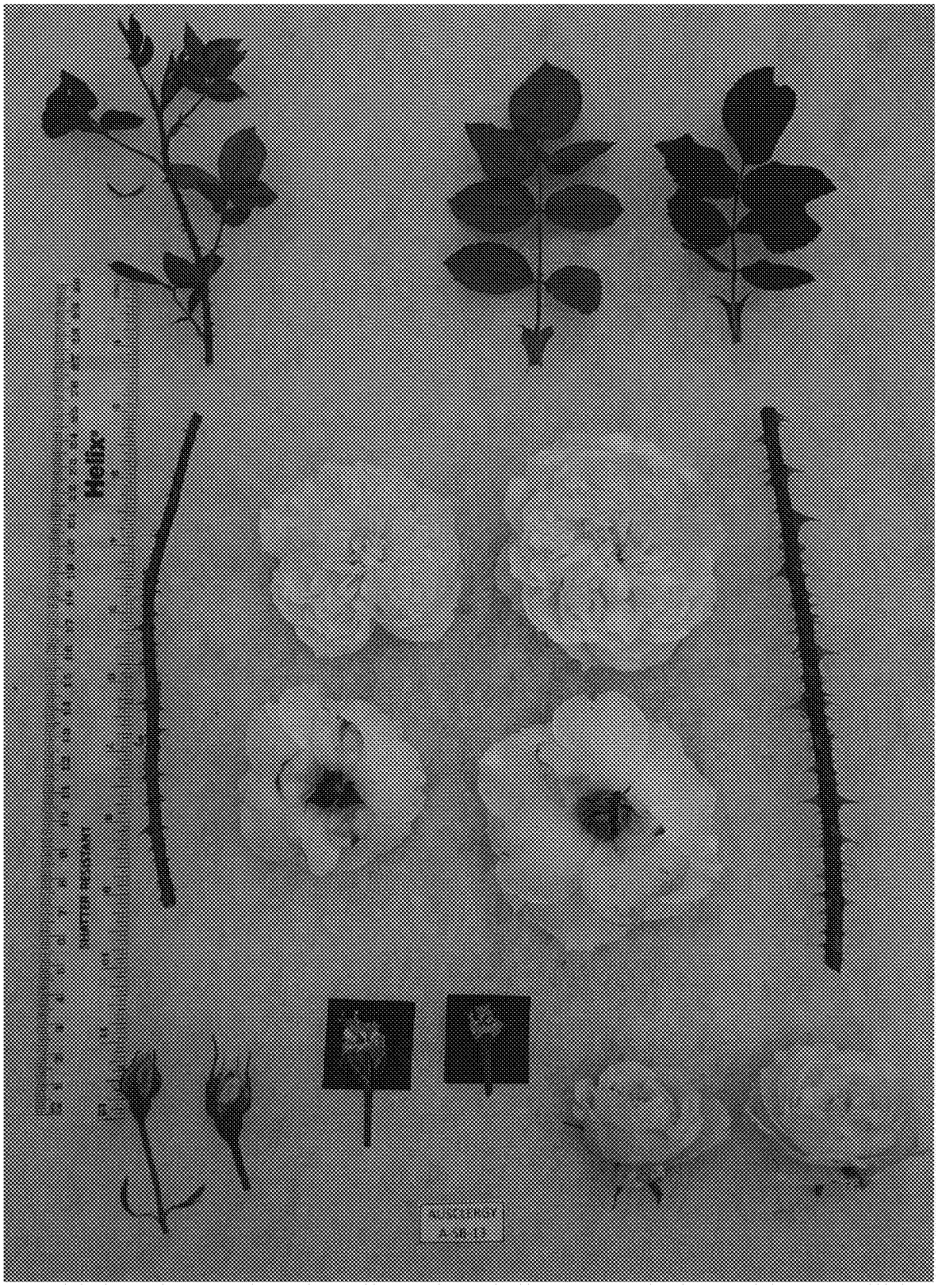
Holly